United States Patent
Pfaff et al.

(10) Patent No.: US 6,517,628 B1
(45) Date of Patent: *Feb. 11, 2003

(54) PIGMENT MIXTURE

(75) Inventors: Gerhard Pfaff, Münster (DE); Ralf Anselmann, Ramsen (DE); Sabine Schoen, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/550,600

(22) Filed: Apr. 17, 2000

(30) Foreign Application Priority Data

Apr. 16, 1999 (DE) .......................... 199 17 388

(51) Int. Cl.⁷ .................. C04B 14/20; C04B 14/04; C09B 67/50; B32B 15/02; B32B 17/02
(52) U.S. Cl. .................. 106/417; 106/415; 106/482; 106/410; 428/404
(58) Field of Search ................ 106/415, 417, 106/410, 482; 428/404

(56) References Cited

U.S. PATENT DOCUMENTS

| | | | | |
|---|---|---|---|---|
| 3,087,828 A | * | 4/1963 | Linton | 106/291 |
| 3,087,829 A | * | 4/1963 | Linton | 106/291 |
| 5,320,781 A | * | 6/1994 | Stahlecker et al. | 252/518 |
| 5,441,564 A | | 8/1995 | Vogt | 106/417 |
| 6,132,873 A | * | 10/2000 | Dietz et al. | 428/404 |
| 6,156,115 A | * | 12/2000 | Pfaff et al. | 106/403 |
| 6,267,810 B1 | * | 7/2001 | Pfaff et al. | 106/415 |
| 6,294,010 B1 | * | 9/2001 | Pfaff et al. | 106/415 |
| 6,334,893 B1 | * | 1/2002 | Pfaff et al. | 106/442 |

FOREIGN PATENT DOCUMENTS

| | | | | |
|---|---|---|---|---|
| DE | WO-93/08237 | * | 4/1993 | C09C/1/00 |
| EP | 0220617 A2 | * | 5/1987 | C09B/63/00 |

* cited by examiner

Primary Examiner—Mark L. Bell
Assistant Examiner—Patricia L. Hailey
(74) Attorney, Agent, or Firm—Millen, White, Zelano & Branigan, P.C.

(57) ABSTRACT

The present invention relates to pigment mixtures comprising at least two components, component A being multilayer pigments based on mica, $SiO_2$ flakes, glass flakes, $Al_2O_3$ flakes or polymer flakes and component B being platelet-shaped, acicular or spherical colorants and/or fillers, and to the use thereof expecially in varnishes, paints, printing inks, powder coatings, plastics, ceramic glazes, polymer films and cosmetic formulations.

19 Claims, No Drawings

PIGMENT MIXTURE

The present invention relates to pigment mixtures comprising at least two components, component A being multilayer pigments based on mica, $SiO_2$ flakes, glass flakes, $Al_2O_3$ flakes or polymer flakes and component B being platelet-shaped, acicular or spherical colorants and/or fillers, and to their use in varnishes, paints, printing inks, plastics, powder coatings, ceramic glazes, polymer films and cosmetic formulations.

BACKGROUND OF THE INVENTION

With platelet-shaped pigments, hiding power and luster are often difficult to realize simultaneously to a satisfactory extent. For instance, $SiO_2$ flakes or mica platelets covered with one or more thin metal oxide layers feature interference colors and a high luster but at the same time, owing to the transparent substrate, also feature high transparency and hence a comparatively poor hiding power.

DE-A-42 40 511 discloses a pigment mixture composed of an interference pigment and a platelet-shaped color pigment. The interference pigment comprises metal oxide-coated mica or $SiO_2$ flakes and the color pigment can be colored $SiO_2$ flakes. This pigment mixture is incorporated into coating materials, printing inks, plastics or cosmetics.

SUMMARY OF THE INVENTION

An object of the present invention is to provide a pigment mixture which is notable for comparatively high hiding power and which lends itself well to incorporation into the respective system in which it is used, and in which, at the same time, pigment/colorant separation in the system is largely ruled out.

Upon further study of the specification and appended claims, further objects and advantages of this invention will become apparent to those skilled in the art.

Surprisingly, a pigment mixture has now been found which has none of the disadvantages indicated above. The pigment mixture of the invention comprises at least two components, component A comprising multilayer pigments based on mica, $SiO_2$ flakes, glass flakes, $Al_2O_3$ flakes or polymer flakes and component B comprising platelet-shaped, acicular or spherical colorants and/or fillers.

By admixing one or more of the described colorants and/or fillers with the multilayer pigments it is possible to provide application systems with a color flop (strongly angle-dependent color), with intensified color effect, and with new kinds of color effects.

The invention therefore provides a pigment mixture comprising at least two components, component A comprising multilayer pigments based on mica, $SiO_2$ flakes, glass flakes, $Al_2O_3$ flakes or polymer flakes and component B comprising platelet-shaped, acicular or spherical colorants and/or fillers.

The invention likewise provides formulations, such as paints, varnishes, printing inks, plastics, powder coatings, ceramic glazes, polymer films and cosmetic formulations, which comprise the pigment mixture of the invention.

The multilayer pigments can be mixed in any proportion with the colorant and/or filler. The weight ratio of component A to component B is preferably from about 1:20 to about 20:1, in particular from about 1:10 to about 10:1.

The multilayer pigments, including those which are known, for example, from the German laid-open specifications DE 196 18 563, DE 196 18 566, DE 196 18 569, DE 197 07 805, DE 197 07 806 and DE 197 46 067 are based on a platelet-shaped, transparent, colored or colorless matrix consisting of mica (synthetic or natural), $SiO_2$ flakes, glass flakes, $Al_2O_3$ flakes, polymer flakes, and possess in general a thickness of preferably from about 0.3 to 5 µm, in particular from about 0.4 to 2.0 µm. The extent in the two other dimensions is preferably from about 1 to 250 µm, more preferably from about 2 to 100 µm, and in particular from about 5 to 40 µm. The multilayer pigments include the matrix (substrate) coated with metal oxides (at least 2). The coating of the substrate flakes of mica, $SiO_2$ flakes, glass flakes or $Al_{2O3}$ flakes with two or more layers is done so as to give a layer structure having alternating layers of high and low refractive index, i.e., at least two adjacent layers where one is of high refractive index and the other of low refractive index. The multilayer pigments preferably contain 2, 3, 4, 5, 6 or 7 layers, especially 3, 4, or 5 layers. The multilayer coating can be provided on one or both sides of the pigment. Examples of suitable metal oxides of high refractive index are titanium dioxide, zirconium oxide, zinc oxide, iron oxides, iron titanium oxides (iron titanates) and/or chromium oxide, especially $TiO_2$ and/or $Fe_2O_3$. Metal oxides of low refractive index which are used include $SiO_2$ and $Al_{2O3}$. However, it is also possible for this purpose to use $MgF_2$ or an organic polymer (e.g. acrylate). The substrate flakes can be coated, for example, as in WO 93/08237 (wet-chemical coating) or DE-A-196 14 637 (CVD process).

Preferred multilayer pigments possess the following structure:

substrate+$Fe_2O_3$ layer+$SiO_2$ layer+$Fe_2O_3$ layer
substrate+$Fe_2O_3$ layer+$SiO_2$ layer+$TiO_2$ layer
substrate+$TiO_2$ layer+$SiO_2$ layer+$Fe_2O_3$ layer
substrate+$TiO_2$ layer+$SiO_2$ layer+$TiO_2/Fe_2O_3$ layer
substrate+$TiO_2/Fe_2O_3$ layer+$SiO_2$ layer+$TiO_2/Fe_2O_3$ layer
substrate+$TiO_2$ layer+$SiO_2$ layer+$Cr_2O_3$ layer Instead of the outer metal oxide layer it is also possible to use a semitransparent layer of a metal. Suitable metals for this purpose are, for example, Cr. Ti, Mo, W, Al, Cu. Ag, Au or Ni.

To obtain specific color effects it is also possible to incorporate fine particles in the nanometer size range into the layers of the multilayer pigment, for example, in either the high and low refractive index layers, respectively. Examples of suitable candidates are finely divided $TiO_2$ or finely divided carbon (e.g., carbon black) with particle sizes from about 10–250 nm. A controlled influence can be exerted on luster and hiding power by virtue of the light-scattering properties of such particles.

In order to improve the light, weathering and chemical stability or to enhance the compatibility in different media, the multilayer pigments can also be provided with a protective layer. Examples of suitable aftercoatings and aftertreatments are the processes described in DE 22 15 191, DE 31 51 354, DE 32 35 017 or DE 33 34 598. The substances applied additionally preferably account for only from about 0.1 to 5% by weight, more preferably from 0.5 to 3.0% by weight of the multilayer pigment.

Suitable components B for the pigment mixture of the invention are all platelet-shaped, acicular and spherical colorants or fillers known to the person skilled in the art, excluding those encompassed by component A. Preferably, they will have a particle size of from about 0.001 to 10 µm, more preferably from about 0.01 to 1 µm. The pigment mixtures of the invention preferably include absorption pigments as colorants and platelet-shaped or spherical powders as fillers. Preferable for component B are coated or uncoated spherical $SiO_2$ particles. $SiO_2$ particles coated with one or more metal oxides are known, for example, from EP 0 803 550 A2.

Preferred pigment mixtures contain in addition to component A, a colorant as component B, in particular a pearl luster pigment. The pearl luster pigments used are preferably pigments based on platelet-shaped, transparent or semitransparent substrates of, for example sheet silicates, such as mica, synthetic mica, talc, sericite, kaolin, glass or other silicatic materials, which are coated with colored or colorless metal oxides such as, for example $TiO_2$, titanium suboxides, titanium oxynitrides, $Fe_2O_3$, $Fe_3O_4$, $SnO_2$, $Cr_2O_3$, ZnO, CuO, NiO and other metal oxides, alone or in a mixture in a uniform layer or in successive layers. However, excluded from such component B colorants are those with multilayer pigments having alternating high and low refractive index encompassed by component A. Pearl luster pigments are known, for example, from the German patents and patent applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are available commercially, for example under the brand name Iriodin® from Merck KGaA, Darmstadt, Germany. Particularly preferred pigment preparations contain $TiO_2$-coated mica, $Fe_2O_3$-coated mica and/or $TiO_2/Fe_2O_3$-coated mica pigments.

Preference is further given to $TiO_2$- and/or $Fe_2O_3$-coated $SiO_2$ or $Al_2O_3$ flakes. The coating of the $SiO_2$ flakes with one or more metal oxides can be done, for example, as described in WO 93/08237 (wet-chemical coating) or DE-A 196 14 637 (CVD process).

Suitable platelet-shaped colorants further include pearl luster pigments based on mica, $SiO_2$ flakes, $Al_2O_3$ flakes or glass flakes which are encased only with one metal oxide layer, metal effect pigments (Al flakes, bronzes), optically variable pigments (OVPs), liquid crystal polymer pigments (LCPs) or holographic pigments.

The spherical colorants include, for example, $TiO_2$, colored $SiO_2$, $CaSO_4$, iron oxides, chromium oxides, carbon black and organic color pigments, such as e.g. anthraquinone pigments, quinacridone pigments, diketopyrrolopyrrole pigments, phthalocyanine pigments, azo pigments and isoindoline pigments. The acicular pigments include, preferably, BiOCl, colored glass fiberes α-FeOOH and organic color pigments, such as e.g. azo pigments, β-phthalocyanine CI Blue 15.3, Cromophtal Yellow 8GN (Ciba-Geigy), Irgalith Blue PD56 (Ciba-Geigy), azomethine copper complex CI Yellow 129, and Irgazine Yellow 5GT (Ciba-Geigy).

The pigment mixture of the invention is simple and easy to handle. The pigment mixture can be incorporated into the system in which it is used by simple stirring. Laborious grinding and dispersing of the pigments is not required.

The pigment mixture of the invention can be used, for example, to pigment paints, printing inks, plastics, agricultural films, seed coatings, food colorings, button pastes, medicament coatings or cosmetic formulations, such as lipsticks, nail varnishes, powder compacts, shampoos, loose powders and gels. The concentration of the pigment mixture in the system in which it is to be used for pigmenting is generally from about 0.1 and 70% by weight, preferably from about 0.1 to 50% by weight and, in particular, from about 1.0 to 10% by weight, based on the overall solids content of the system. This concentration is generally dependent on the specific application.

Plastics comprising the pigment mixture of the invention in amounts of from about 0.01 to 50% by weight, in particular from about 0.1 to 7% by weight, are frequently notable for a particular color flop effect, or else for a sparkle effect.

In the coatings sector, especially in automotive finishing, the pigment mixture is used, for example, for three-coat systems in amounts of 0.1–10% by weight, preferably from 1 to 3% by weight.

The proportion in which the multilayer pigments are mixed with component B depends on the desired effect. The multilayer pigments, component A, are preferably used with component B in a weight ratio of from about 10:1 to 1:10.

In a coating material, the pigment mixture of the invention has an advantage that the desired color flop effect is obtained by a single-coat system (one-coat system or base coat in a 2-coat system). This color flop is extremely pronounced even under diffuse light. In comparison with coatings comprising a mica-based interference pigment instead of the multilayer pigments, coatings with the pigment mixture of the invention exhibit a more distinct depth effect and a glitter effect.

The pigment mixture of the invention can also be used to advantage in decorative and care cosmetics. The concentration in which it is used and the proportion in which multilayer pigments are mixed with component B, especially organic and inorganic color pigments and dyes, of natural or synthetic origin, such as chromium oxide, ultramarine, spherical $SiO_2$ or $TiO_2$ pigments, for example, are dependent on the application medium and on the effect that is to be obtained. Multilayer pigments can be mixed with other pigments or dyes in any proportion; preferably, the ratio is from 1:10 to 10:1. The concentration in which the mixture is used ranges from 0.01% by weight in a shampoo up to 70% by weight in a compact powder. In the case of a mixture of multilayer pigments with spherical fillers, e.g. $SiO_2$, the concentration in the formulation can be 0.01–70 % by weight. The cosmetic products, such as nail varnishes, lipsticks, compact powders, shampoos, loose powders and gels, for example, are notable for particularly interesting luster effects and/or color effects, which depending on the structure of the multilayer pigment may be strongly angle-dependent. The glitter effect in nail varnish can be increased significantly relative to conventional nail varnishes by using the pigment mixtures of the invention. Furthermore, the pigment mixture of the invention can be used in bath additives, in toothpastes and to enhance food products, e.g. as a mass coloring or as a coating.

In the case of the pigmentation of binder systems, for example, for paints and printing inks for gravure, offset or screen printing, or as precursors for printing inks, in the form, for example, of highly pigmented pastes, granules, pellets, etc., pigment mixtures consisting in particular of multilayer pigments with spherical colorants, such as $TiO_2$, carbon black, chromium oxide, iron oxide and also organic "color pigments", for example have proven to be particularly suitable. In general, the pigment mixture is incorporated into the printing ink in amounts of 2–35% by weight, preferably 5–25% by weight, and in particular 8–20% by weight. Offset printing inks may contain the pigment mixture in amounts of up to 40% by weight or more. The precursors for the printing inks, e.g. in granule form, as pellets, briquettes, etc., contain not only the binder and additives but also up to 95% by weight of the pigment mixture of the invention. The mixing ratio of component A to component B is preferably in the range from 1:10 to 10:1. The printing inks containing the pigment mixture of the invention exhibit purer hues and are of improved printability owing to the good viscosity values.

The invention therefore also provides formulations comprising the pigment mixture of the invention.

The examples which follow are intended to elucidate the invention without, however, limiting it. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 17 388.5, filed Apr. 16, 1999, is hereby incorporated by reference.

EXAMPLES

Example 1

Printing Ink

The pigment was stirred at 600 rpm into the solvent-containing binder and the printing inks were subsequently knife-coated onto black-white cards.

Ink No. 1

88.0 g of Gebr. Schmidt 95 MB 011 TW (nitrocellulose binder)

10.0 g of multilayer pigment consisting of mica flakes of particle size 5–40 $\mu$m, coated on both sides with 3 layers in the following sequence: $Fe_2O_3$, $SiO_2$, $Fe_2O_3$ 2.0 g of Gebr. Schmidt 95 MB 022-TW (binder with green colorant)

Ink No. 2 Comparative 88.0 g of Gebr. Schmidt 95 MB 011 TW (nitrocellulose binder)

10.0 g of $Fe_2O_3$-coated mica of particle size 10 to 60 $\mu$m (from Merck KGAA)

2.0 g of Gebr. Schmidt 95 MB 022-TW (binder with green colorant)

The color card with ink No. 1 shows a much better color flop, visually, than the color cards with the comparative ink No. 2.

Example 2

Car Paint

| | |
|---|---|
| 2.0 g | $SiO_2$ flakes of particle size 5–40 $\mu$m, coated on both sides with 3 layers in the following sequence: $Fe_2O_3$, $SiO_2$, $Fe_2O_3$ |
| 1.5 g | Heliogen Blue L 6930 (phthalocyanine pigment) |
| 0.2 g | Hostaperm green 8G (phthalocyanine pigment) |
| 0.05 g | Pigment-grade carbon black FW 200 |
| 66.6 g | base coat (A4) MP system (SC = 19%) |
| 29.65 g | diluent mixture |

A hue of a strongly pronounced blue-green flop and golden highlights is obtained, which can even change in the dark-violet direction.

Example 3

Plastic

The granular plastics polypropylene PP Stamylan PPH10 (from DSM) and, respectively, polystyrene 143E (from BASF) are admixed in each case with a) 1% $SiO_2$ flakes of particle size 5–40 $\mu$m, coated on both sides with 3 layers in the following sequence: $Fe_2O_3$, $SiO_2$, $Fe_2O_3$ b) a mixture of 1% $SiO_2$ flakes of particle size 5–40 $\mu$m, coated on both sides with 3 layers in the following sequence: $Fe_2O_3$, $SiO_2$, $Fe_2O_3$; and 0.1% PV-Echtblau B2G01 (Pigment Blue 15.3 from Clariant; phthalocyanine pigment)

c) 1% $Fe_2O_3$-coated mica of particle size 10–60 $\mu$m (Merck KGaA)

d) a mixture of 1% $Fe_2O_3$-coated mica of particle size 10–60 $\mu$m (Merck KGaA) and 0.1% PV-Echtblau B2G01 (Pigment Blue 15.3 from Clariant; phthalocyanine pigment).

The pigmented granules are subsequently processed on an injection molding machine to give small stepped plaques.

When using the pigment under a) and in the case of the mixture under b), a strongly angle-dependent color is achieved in the plastic. This color is much more highly variable in the case of b) and can be used, for example, for a vigorous blue-green flop.

Example 4

Eyeshadow

| | |
|---|---|
| Phase I | |
| 5.00 % | silica |
| 25.00 % | $SiO_2$ flakes of particle size 5–40 $\mu$m coated with 3 layers in the following sequence: $Fe_2O_3$, $SiO_2$, $Fe_2O_3$ |
| 5.00 % | C.I. Pigment Green 18 (CI77289; chromium hydroxide pigment) |
| 47.42 % | talc |
| 7.18 % | solanum tuberosum (potato starch) |
| 2.40 % | magnesium stearate |
| Phase II | |
| 6.96 % | isopropyl stearate |
| 0.40 % | cetyl palmitate |
| 0.40 % | petrolatum |
| 0.08 % | preservative |

The components of phase I are combined and formed into a premix. The melted phase II is then added dropwise with stirring to the powder mixture. The powders are pressed at 40–50 bar.

The eyeshadow obtained is distinguished by an intense luster and a color which changes greatly according to the viewing angle.

Example 5

Lipstick

| | |
|---|---|
| Phase I | |
| 8.25 % | cera alba |
| 4.95 % | ceresin Copernica cerifera |
| 3.30 % | lanolin oil |
| 5.28 % | isopropyl myristate |
| 1.98 % | mineral oil |
| 0.03 % | tocopherol, ascorbyl palmitate, ascorbic acid, citric acid, PEG-8 |
| 0.06 % | preservative |
| 0.50 % | flavouring |
| 1.00 % | lithalrubin BK, C.I. Pigment Red 57:1 (CI 15850; organic color pigment) ad 100.00% Ricinus communis (20% in castor oi1) |
| Phase II | |
| 2.00 % | silica |
| 15.00 % | $SiO_2$ flakes of particle size 5–40 $\mu$m coated with 3 layers in the following sequence: $Fe_2O_3$, $SiO_2$, $Fe_2O_3$ |

The components of phase I are heated to 75° C. and melted. The pigments of phase II are added and all the components are stirred together thoroughly. The lipstick mass is then stirred for 15 min in the casting apparatus, which has been conditioned to a temperature of 65° C. The homogenous melt is poured into the casting molds, which are preheated to 65° C. Subsequently, the molds are cooled and the moldings are removed cold.

The lipstick is distinguished by an intense luster and a color which changes strongly depending on the viewing angle.

Example 6
Shower Gel

| Phase A | |
|---|---|
| 0.10 % | mica pigment of particle size 10–60 μm, coated on both sides with $TiO_2$, $SiO_2$, $TiO_2$ (1) |
| 0.75 % | xanthan gum (2) |
| 62.10 % | water |
| Phase B | |
| 20.00 % | decyl glucoside (3) |
| 6.65 % | Texapon ASV (sodium laureth sulfate, magnesium laureth sulfate, sodium laureth 8-sulfate, magnesium laureth B-sulfate, sodium oleth sulfate, magnesium oleth sulfate) (3) |
| 0.20 % | Bronidox L (propylene glycol, 5-bromo-5-nitro-1,3-dioxane) (3) |
| 0.05 % | fragrance (fragrance oil Everest 79658 SB) (4) |
| Phase C | |
| 0.15 % | citric acid (1) |
| 0.10 % | Sicovit Green Z 6120 (organic color pigment mixture) (1% strength in water) [CI 19140/42051] (5) |
| 10.00 % | water |

Sources:
(1) Merck KGaA
(2) Monsanto
(3) Henkel KGaA
(4) Haarmann & Reimer
(5) BASF For phase A, the pigment is stirred into water. Xanthan gum is scattered slowly into the suspension with stirring, and stirring is continued until the gum has dissolved. Phases B and C are added in succession and then stirring is continued until all of the components are homogenously dispersed.

The shower gel is distinguished by intense interference glitter effects.

Example 7
Eyeliner Gel

| Phase A | |
|---|---|
| 15.00 % | mica pigment of particle size 10–60 μm, coated on both sides with $TiO_2$, $SiO_2$, $TiO_2$ (1) |
| 5.0 % | mica pigment of particle size 10–60 μm coated with $Fe_3O_4$ (1) |
| 2.00 % | Ronasphere ® (silica) (1) |
| 0.40 % | Carbopol ETD 2001 (carbomer) (2) |
| q.s. | citric acid (1) |
| 60.00 % | water |
| Phase B | |
| 4.0 % | glycerol (1) |
| 0.90 % | triethanolamine (1) |
| 2.00 % | Luviskol VA 64 powder (PVP/VA copolymer) (3) |
| 0.20 % | Germaben II (propylene glycol, diazolidinyl urea, methylparaben, propylparaben) (4) |
| ad 100.00 % | water |

Sources
(1) Merck KGaA
(2) BF Goodrich
(3) BASF
(4) ISP Europe

The pigments and Ronasphere® are dispersed in the water of phase A. Using a few drops of citric acid solution, the pH is adjusted to 3.8 in order to reduce the viscosity. Carbopol is scattered in with stirring. After complete dissolution, the predissolved phase B is stirred in slowly.

The product obtained is distinguished by high luster and an intense interference color.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment mixture comprising: a component A comprising a mica, $SiO_2$ flake, glass flake, $Al_2O_3$ flake or polymer flake substrate coated with two or more layers including at least one layer of high refractive index adjacent to at least one layer of low refractive index and component B comprising a platelet-shaped, acicular or spherical colorant and/or filler not within the definition of component A.

2. A pigment mixture according to claim 1, wherein component A comprises a multilayer pigment having an $SiO_2$ flake, mica flake, glass flake, or $Al_2O_3$ flake substrate coated with alternating layers of metal oxides of high and low refractive index.

3. A pigment mixture according to claim 2, wherein the multilayer pigment comprises as at least one layer of high refractive index a $TiO_2$, $Fe_2O_3$, ZnO or $ZrO_2$ layer.

4. A pigment mixture comprising: a component A which comprises a multilayer pigment having an $SiO_2$ flake, mica flake, glass flake, or $Al_2O_3$ flake substrate coated with alternating layers of metal oxides of high and low refractive index, having as at least one layer of low refractive index a $SiO_2$, or $Al_2O_3$ layer, and a component B comprising a platelet-shaped, acicular or spherical colorant and/or filler not within the definition of component A.

5. A pigment mixture comprising, a component A comprising a mica, $SiO_2$ flake, glass flake, $Al_2O_3$ flake or polymer flake substrate coated with two or more layers including at least one layer of high refractive index adjacent to at least one layer of low refractive index and a component B comprising a platelet-shaped, acicular or spherical colorant and/or filler not within the definition of component A, wherein component A comprises a multilayer pigment having an $Fe_2O_3$—$SiO_2$—$Fe_2O_3$ multilayer coating, a ($TiO_2$/$Fe_2O_3$)—$SiO_2$—($TiO_2$/$Fe_2O_3$) multilayer coating or a $TiO_2$—$SiO_2$—$TiO_2$ multilayer coating.

6. A pigment mixture according to claim 1, wherein component B comprises pearl luster pigments, colored glass particles, carbon black, organic color pigments and/or inorganic color pigments.

7. A pigment mixture according to claim 1, wherein component A and component B are mixed in a weight ratio of from 10:1 to 1:10.

8. A paint, varnish, printing ink, plastic, powder coating, for coloring seed, cosmetic or food product composition comprising a pigment mixture according to claim 1.

9. The composition of claim 1 which is a varnish for automotive finishing.

10. A pigment mixture according to claim 1, wherein the component A comprises 2 to 7 coating layers.

11. A pigment mixture according to claim 1, wherein the component A is a multilayer pigment of one of the following structures:

substrate+$Fe_2O_3$ layer+$SiO_2$ layer+$Fe_2O_3$ layer,
substrate+$Fe_2O_3$ layer+$SiO_2$ layer+$TiO_2$ layer,
substrate+$TiO_2$ layer+$SiO_2$ layer+$Fe_2O_3$ layer,
substrate+$TiO_2$ layer+$SiO_2$ layer+$TiO_2$/$Fe_2O_3$ layer,
substrate+$TiO_2$/$Fe_2O_3$ layer+$SiO_2$ layer+$TiO_2$/$Fe_2O_3$ layer, or
substrate+$TiO_2$ layer+$SiO_2$ layer+$Cr_2O_3$ layer.

12. A pigment mixture according to claim 1, wherein the component A is a multilayer pigment having an outer layer of a semitransparent layer of a metal selected from Cr, Ti, Mo, W, Al, Cu, Ag, Au or Ni.

13. A pigment mixture according to claim 1, wherein component B comprises colorant and/or filler particles having a particle size of from about 0.001 to 10 μm.

14. A pigment mixture according to claim 1, wherein component B comprises absorption pigments as colorants and platelet-shaped or spherical powders as fillers.

15. A pigment mixture according to claim 1, wherein component B comprises coated or uncoated spherical $SiO_2$ particles.

16. A pigment mixture according to claim 1, wherein component B comprises a pearl luster pigment, not within the definition of component A.

17. A pigment mixture according to claim 1, wherein component B comprises a platelet-shaped colorant selected from the group consisting of pearl luster pigments based on mica, $SiO_2$ flakes, $Al_2O_3$ flakes or glass flakes which are encased only with one metal oxide layer, metal effect pigments, optically variable pigments, liquid crystal polymer pigments and holographic pigments.

18. A pigment mixture according to claim 1, wherein component B comprises a spherical colorant selected from the group consisting of $TiO_2$, colored $SiO_2$, $CaSO_4$, iron oxides, chromium oxides, carbon black and spherical organic color pigments.

19. A pigment mixture according to claim 1, wherein component B comprises an acicular pigment selected from the group consisting of BiOCl, colored glass fibers, α-FeOOH and acicular organic color pigments.

* * * * *